United States Patent [19]

Maumy et al.

[11] Patent Number: 5,735,901

[45] Date of Patent: Apr. 7, 1998

[54] ELEMENT FOR TEMPORARILY INCREASING THE RIGIDITY OF AN ORTHOPAEDIC PROSTHESIS

[75] Inventors: Jean Maumy, Montauban, France; Roland Baege, Wiesendangen, Switzerland

[73] Assignee: Sulzer Medizinaltechnik AG, Winterthur, Switzerland

[21] Appl. No.: 657,453

[22] Filed: May 29, 1996

Related U.S. Application Data

[62] Division of Ser. No. 287,548, Aug. 8, 1994, abandoned.

[30] Foreign Application Priority Data

Aug. 30, 1993 [EP] European Pat. Off. ............. 93810617

[51] Int. Cl.⁶ .................................................. A61F 2/30
[52] U.S. Cl. ............................. 623/18; 623/22; 623/23
[58] Field of Search ................................... 623/18, 19, 20, 623/22, 23

[56] References Cited

U.S. PATENT DOCUMENTS

| | | | |
|---|---|---|---|
| 4,329,743 | 5/1982 | Alexander et al. | 3/1 |
| 5,092,896 | 3/1992 | Meuli et al. | 623/21 |
| 5,116,357 | 5/1992 | Eberbach | 606/213 |
| 5,163,960 | 11/1992 | Bonutti | 623/16 |
| 5,192,331 | 3/1993 | Spotorno et al. | 623/23 |
| 5,201,738 | 4/1993 | Scott et al. | 606/77 |
| 5,207,712 | 5/1993 | Cohen | 623/21 |
| 5,310,408 | 5/1994 | Schryver et al. | 623/22 |
| 5,360,450 | 11/1994 | Giannini | 623/21 |

FOREIGN PATENT DOCUMENTS

| | | |
|---|---|---|
| 0 176 711A1 | 9/1984 | European Pat. Off. . |
| 0 321 389A1 | 12/1987 | European Pat. Off. . |
| 0 346 270A1 | 6/1988 | European Pat. Off. . |
| 0 404 716A1 | 6/1989 | European Pat. Off. . |
| 0 495 341A1 | 1/1991 | European Pat. Off. . |
| 0 445 068A1 | 2/1991 | European Pat. Off. . |
| WO 93/ 08770 | 5/1993 | European Pat. Off. . |
| 3322978A1 | 6/1983 | Germany . |
| WO 85/ 05027 | 11/1985 | Germany . |

Primary Examiner—Michael J. Milano
Attorney, Agent, or Firm—Townsend and Townsend and Crew LLP

[57] ABSTRACT

The element (20) according to the invention comprises a biodegradable body which is before or during the implantation of an orthopaedic prosthesis (1) inserted into a recess (2) in the prosthesis (1) such that the rigidity of the prosthesis is increased. The element (20) provides mechanical connection between the shell segments (1a, 1b, 1c) so that the element (20) performs a supporting function which reduces the elastic properties or the possibilities of movement of the outer shell (1). The ability of the biodegradable element (20) to transfer forces is increasingly reduced after the implantation so that the outer shell (1) of the artificial acetabulum has increasingly more elastic properties depending on the mechanical properties determined by the structure. Some time after the implantation, the biodegradable element (20) degrades so much that it no longer transfers any forces.

8 Claims, 3 Drawing Sheets

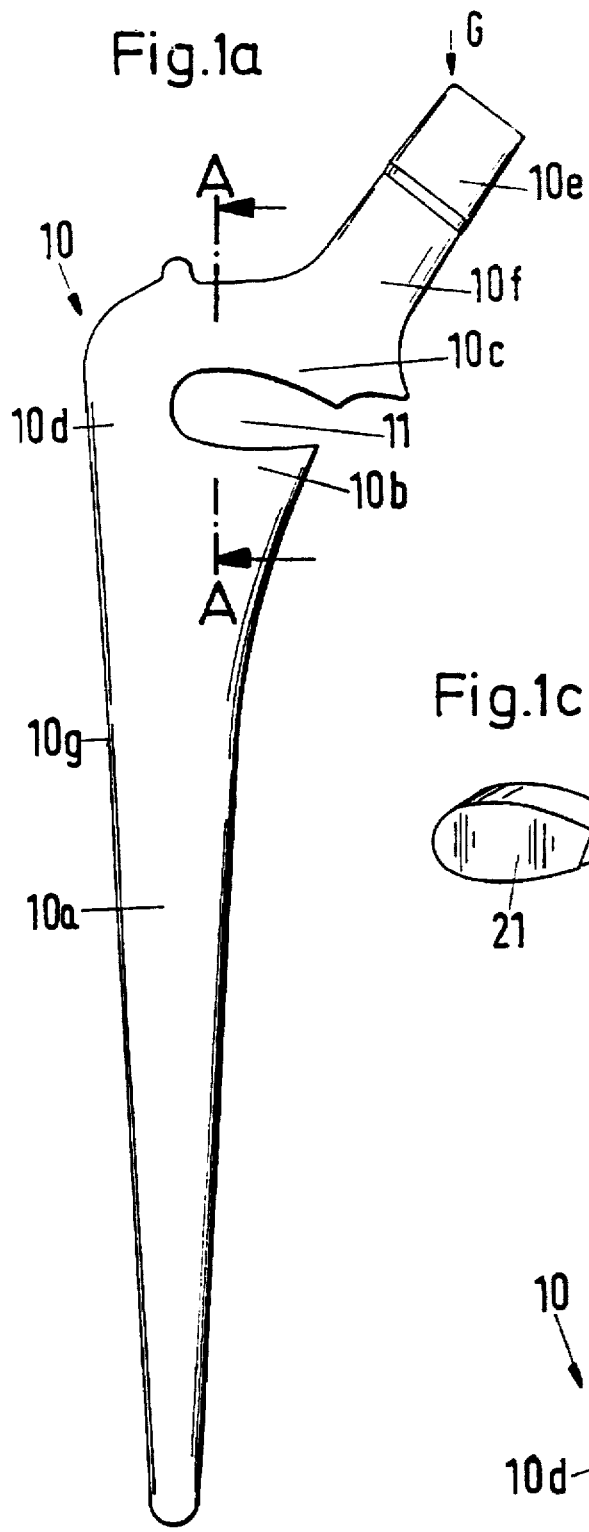
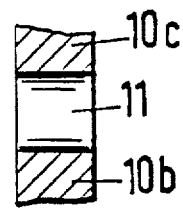
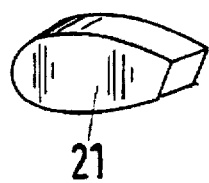
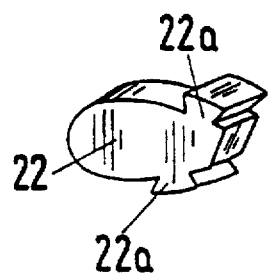
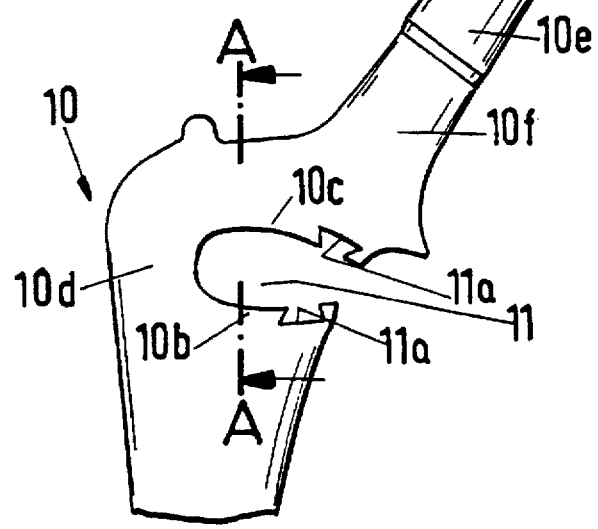

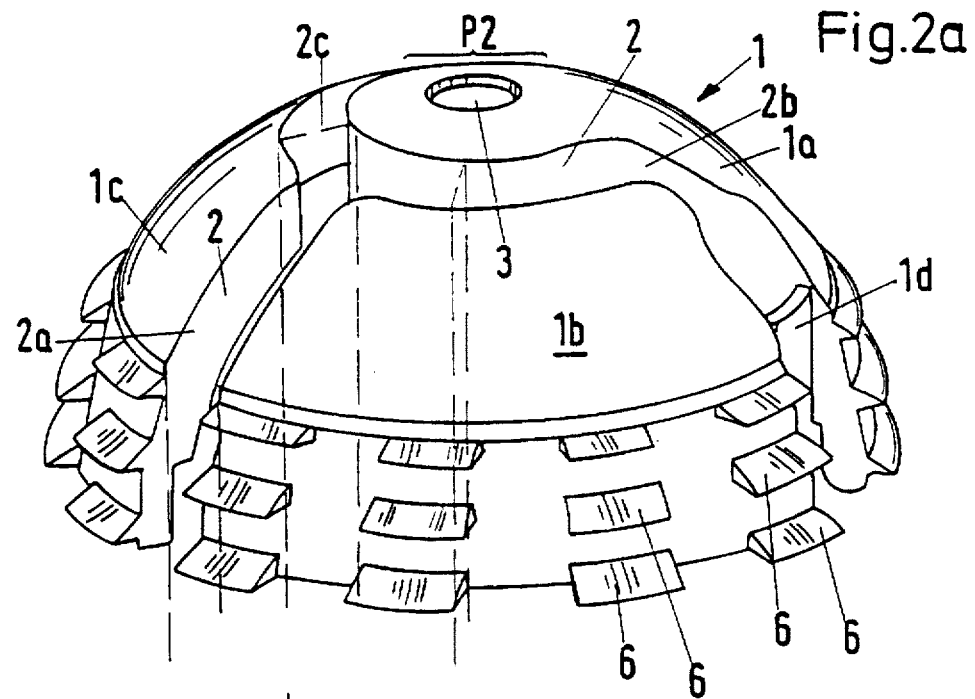
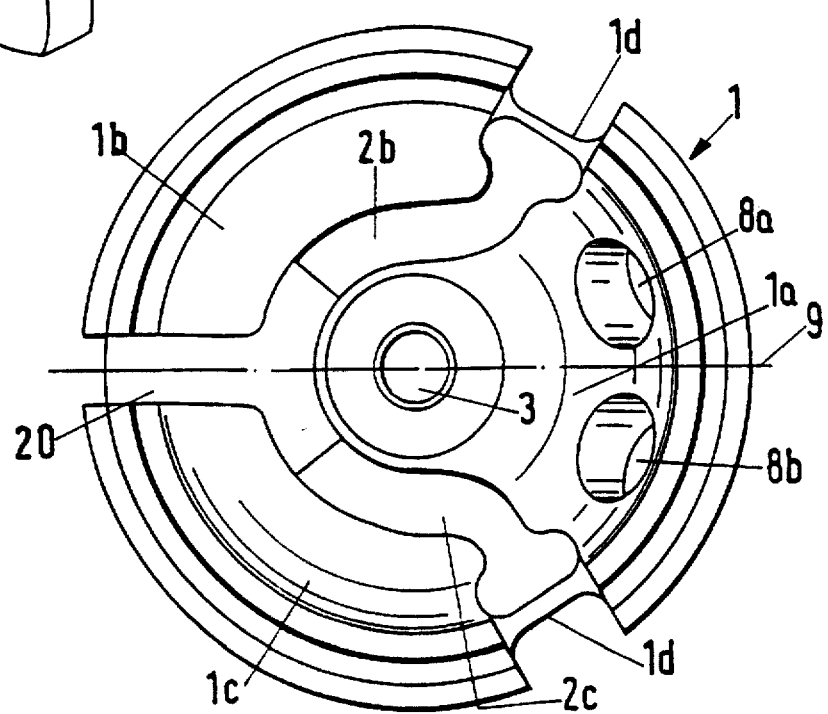

ELEMENT FOR TEMPORARILY INCREASING THE RIGIDITY OF AN ORTHOPAEDIC PROSTHESIS

This is a Division of application No. 08/287,548 filed Aug. 8, 1994 now abandoned.

The invention relates to an element for temporarily increasing the rigidity of an orthopaedic prosthesis according to claim 1. It also relates to orthopaedic prostheses comprising an element according to the invention.

From EP 0 445 068 A1 is known an orthopaedic prosthesis, particularly for an artificial acetabulum, which is composed of an inner shell and an outer shell, the wall thickness of the outer shell being much thinner than the wall thickness of the inner shell. The metallic outer shell is kept so thin that, on the one hand, it can elastically adapt, after growing-in of the osseous tissue, to small changes of the osseous tissue. On the other hand, forces are transferred from the relatively rigid metallic inner shell onto the outer shell so that the outer shell is deformed according to the reaction forces in the osseous tissue and according to its rigidity.

The elastic properties of an orthopaedic prosthesis can prove to be disadvantageous during a limited period immediately after the implantation. The elastic properties can, for instance, hamper growing of the bone onto the prosthesis. Also the known artificial acetabulum has the disadvantage that the outer shell can deform, in adverse circumstances, particularly under the influence of relatively high forces, which may delay or impede growing of the osseous tissue into the outer surface of the outer shell.

The aim of the invention is to devise an element which gives to an orthopaedic prosthesis for a limited time increased rigidity.

This aim is achieved according to the invention by the features of claim 1. The subsidiary claims relate to further advantageous embodiments of the element according to the invention.

The element according to the invention comprises a biodegradable body which is inserted before or during implantation of the orthopaedic prosthesis into a recess in the prosthesis in such a way, that the rigidity of the prosthesis is increased. So, for instance, a degradable element may be inserted into the space between the inner and outer shell of the artificial acetabulum known from EP 0 445 068, so that the element has a supporting function. The element provides mechanical connection between the inner and outer shell and thus provides an additional mechanical coupling between the inner and outer shell, which reduces the elastic properties or possibilities of movement of the outer shell. After the implantation the ability of the biodegradable element to transfer forces is increasingly reduced, so that the outer shell of the artificial acetabulum has increasingly more elastic properties, corresponding to the mechanical properties which stem from the structure. Some time after the implantation the biodegradable element becomes so degraded that it no longer transmits any forces. The advantage of the element according to the invention resides primarily in that it gives to the orthopaedic prosthesis increased rigidity during a period following immediately after the implantation and thereby, for instance, reduces relative movement on the surface between the bone and the prosthesis. During a fairly long period after the implantation the element biologically degrades so that the rigidity of the prosthetic device is increasingly reduced and the elastic behaviour, which is desired after completed growing-in, is obtained. A further advantage lies in that no further surgical treatment is needed to remove the element.

The invention will now be described, by way of example, with reference to embodiments. In the drawings:

FIG. 1a is a side elevation of a shaft of a joint endoprosthesis;

FIG. 1b is a section through the prosthesis along the line A—A;

FIG. 1c shows an element for increasing rigidity;

FIG. 1d shows a yoke-shaped portion of a further joint endoprosthesis;

FIG. 1e shows a further embodiment of an element for increasing rigidity;

FIG. 2a shows an outer shell of an artificial acetabulum;

FIG. 2b shows an element for increasing rigidity;

FIG. 2c is a view from below onto an outer shell of an artificial acetabulum;

Figure 3A:
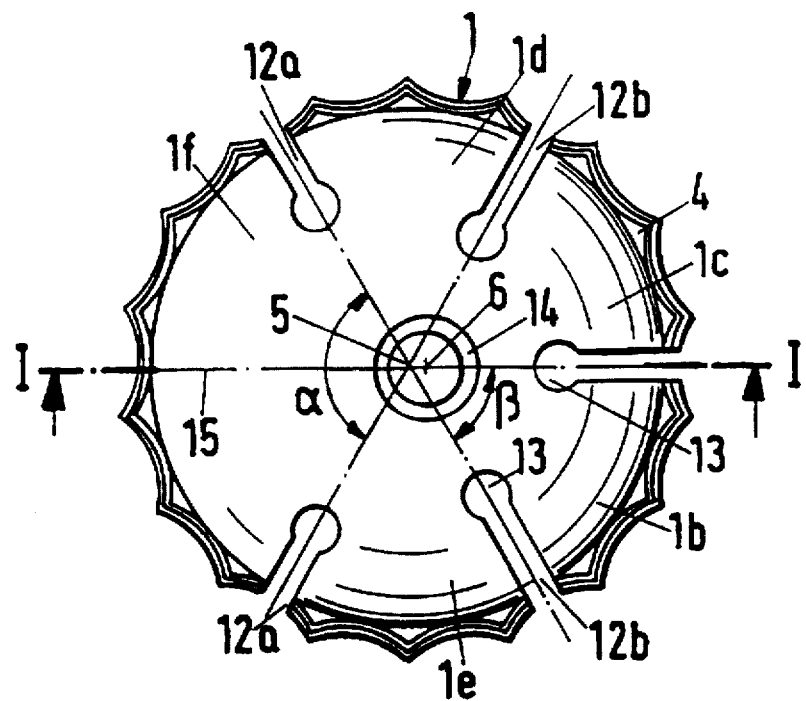
FIG. 3a is a plan view of a further outer shell of an artificial acetabulum.

FIG. 1a is a side view of a joint endoprosthesis 10. The straight shaft 10a widens conically from its distal to its proximal end. The lateral narrow side 10g extends in an arc to a horizontal shoulder on the proximal shaft end, which in turn changes into a prosthesis neck 10f. The latter carries a conical pin 10e for the reception of a joint head (not shown). The shaft 10a forms in the region of the arc and of the horizontal shoulder a yoke-shaped portion which comprises a recess 11. The recess 11 is delimited by two adjacent regions 10b, 10c and an elastically resilient region 10d. When a weight G acts intermittently this causes a small bending in the yoke-shaped portion and consequently damping of the force acting in distal direction, so that loading intermittently may be transmitted onto the osseous tissue without local peaks in tension. At the same time the bending forces, which act in a transverse plane and are transmitted from the prosthesis on the osseous tissue, increase. The forces generated by the resilient properties of the yoke-shaped portion may make the growing of the osseous tissue to the prosthesis more difficult.

A vertical section along line A—A is shown in FIG. 1b from which are apparent the recess 11 in the yoke-shaped portion and also the two adjacent regions 10b, 10c. The resilient elastic behaviour in the yoke-shaped portion between the prosthesis shaft 10a and prosthesis neck 10f may be varied within a wide range depending on the shape of the recess 11. A biodegradable element 21, shown in FIG. 1c, is shaped to correspond to the recess 11 so that the element 21 may be inserted before or during the implantation of the prosthesis 10 into the recess 11 to be there retained by shape or friction. Not illustrated, but obvious, is a complementary shaping of the adjacent regions 10b, 10c and of the element 21, such that the element 21 may be fixed in the recess 11, for instance by grooves and projections made therein, so that the element 21 snaps into the recess 11. The load-bearing ability of the element 21 depends on the used material and causes reduction of resilience in the yoke-shaped portion, or in the transition between the prosthesis shaft 10a and prosthesis neck 10f so that the rigidity of the whole prosthesis 10 is increased. The element 21, shown in FIG. 1c, may be loaded only in compression. In FIG. 1e is shown a further element 22 which comprises engagement elements 22a positioned in the recesses 11a of the prosthesis 10 shown in FIG. 1d in such a way, that the element 22 may be loaded both in tension and in compression.

The bodies 21, 22 are of a biocompatible, biologically resorbable polymer. Such resorbable polymers and copolymers are known from literature and include e.g. polylactic acid, polyglycolic acid, polydioxanone, polycaprolactone and bone-growth factors. If desired, the bodies 21, 22 may be provided with osteogenic inorganic additives such as hydroxyapatite or calcium phosphate for controlled growing into the pores produced by the degraded polymer. To the polymers may also be added antibiotics or bone growth stimulating pharmaceutical agents, such as etidronate, to avoid osteoporosis.

In FIG. 2b is illustrated a further biocompatible biologically resorbable or biodegradable element 20 which serves to reduce the elastic properties of an outer shell 1 (shown in FIGS. 2a and 2c) of an acetabulum during a period following the implantation. FIGS. 2a and 2c show a metallic outer shell 1 which is formed substantially by an attachment zone 1a and two outer shell segments 1b and 1c connected by means of resilient connection elements 1d to the attachment zone 1a. The attachment zone 1a may be primarily anchored in osseous tissue by attachment means, such as spines 6 or bone screws, which extend through the bores 8a, 8b. In the area of the pole P2 is provided a centering or guiding bore 3 to which may be attached the inner shell. The outer shell 1 has recesses 2 which cause the outer shell 1 to be elastically compressible or expandable, particularly in peripheral direction, and has resilient, elastic properties which may be disadvantageous during the phase of growing of the osseous tissue onto the outer shell 1. In order to reduce the elasticity of the outer shell 1, elements 20 may be inserted into the recess 2 to be retained therein by shape or friction. In the present embodiment the outer shell 1 has two S-shaped recesses 2b, 2c between the attachment zone 1a and the outer shell segments 1b, 1c, and also a radial recess 2, extending in the direction of a meridian circle between the outer shell segments 1b and 1c. As is shown in FIG. 2a, the element 20 may be inserted into the recess 2, and the element 20 and the outer shell 1 may be provided with means to define mutual position, for instance such that the element 20 snaps into the outer shell 1. After the implantation, the element 20 is biologically degraded so that, a fairly long time after the implantation, the elastic behaviour of the outer shell 1 is no longer influenced by the element 20.

Figure 3B:
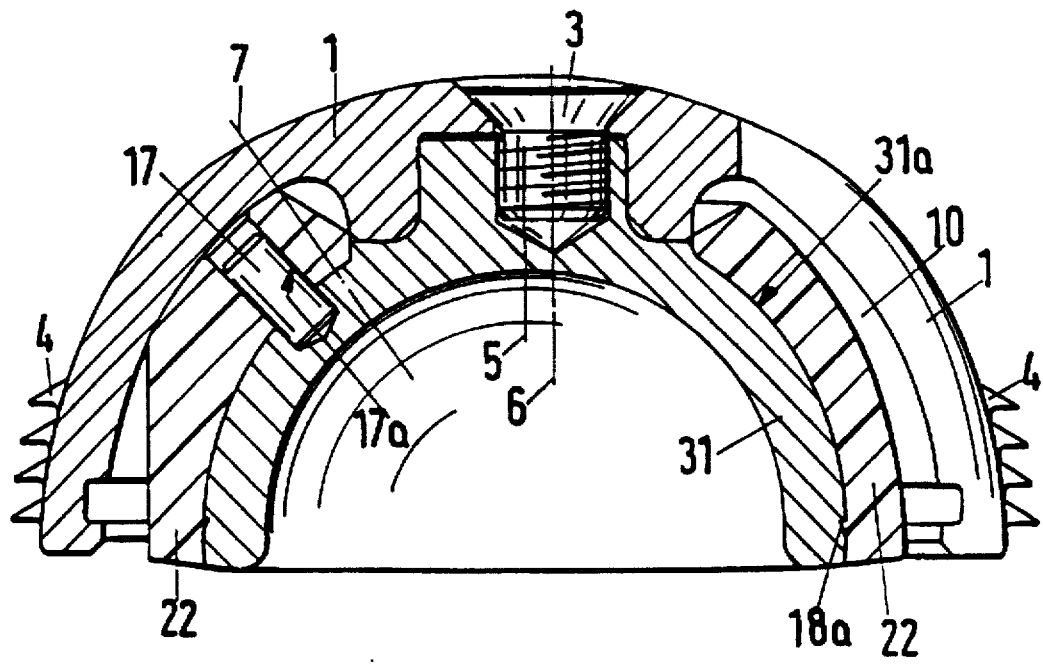
FIG. 3b is a side view of a section (I—I) through the acetabulum.

FIGS. 3a and 3b show a further embodiment of an acetabulum which obtained temporarily increased rigidity by a biodegradable element 22. FIG. 3a is a plan view of an outer shell in the direction of an assembly axis 5. The outer shell 1 has meridian recesses 12a, 12b distributed along its periphery which begin with a circular widening 13 and extend up to the equator of the outer shell 1, so that the outer shell 1 is in the region of the equator discontinuous in the peripheral direction. The meridian recesses 12a, 12b divide the outer shell 1 into shell segments 1b–1f, the shell segments 1b–1e subtending an identical angle β while the shell segment if subtends an angle α which is nearly twice as large as the angle β. In the region of the direction 7 of the main load is arranged the shell segment if which has an increased surface, because the largest forces are transferred onto the bone in this area. The inner shell 31 is connected in the direction of the assembly axis 35 by a connection element 3 to the outer shell 1, the axis 6 of the connection element 3 being offset with respect to the assembly axis 5. The elasticity of the outer shell 1, or the behaviour during the action of static and dynamic forces, may be varied within a wide-scope by the thickness of the outer shell 1 and by the arrangement of the meridian recesses 12a, 12b on the periphery and also by their length. The outer shell is usually made symmetrical with respect to a plane of symmetry along the sectional plane I—I.

From the side view of the acetabulum along the sectional plane I—I is visible in FIG. 3b, between the inner shell 31 and the outer shell 1, a space 10 which is partly filled-in with a biodegradable element 22 in the shape of a spherical cap. The element 22 bears onto the outer surface 31a of the inner shell 31, while the element 22 has, in the region of the equator, a projection 18b, and the inner shell 31 has a notch 18a, so that the element 22 may be attached to the inner shell 31 by snap fastening means formed in this way. It is also possible to make in the inner shell 31 and in the element 22 a recess 17a for a connection element 17 to avoid relative twisting between the inner shell 31 and the element 22. The element 22 is shaped in the region of the direction 7 of the main load or in the region of the shell segment if such that it bears both on the inner shell 31 and on the outer shell 1. A part of the force exerted by the head of the ball-end-socket joint onto the inner shell 1 can thereby be transmitted through the element 22 onto the outer shell 1. The static and dynamic behaviour of the force transfer between the inner shell 31 and outer shell 1 may be influenced by the elasticity and also the shape of the element 22. In the region of the segment 1c the element 22 does not fill-in the whole interspace 10 while the element 22 bears onto the inner shell 1. In this region the element 22 does not influence the transmission of forces between the inner shell 31 and the segment 1c except that the element 22 could limit the maximum deflection of the segment 1c. An element 22 may also be used to fill the interspace 10 completely or at least seal it perfectly from outside, so that the space 10 is closed. The element 22 may also be shaped such that, in addition to the interspace 10, it also partly or completely fills-in the recesses 12a, 12b extending in meridian direction. During a period following the implantation, the biodegradable element 22 gives to the acetabulum increased rigidity. With increasing degradation of the element 22 the acetabulum regains its elastic properties.

The illustrated embodiments of biodegradable elements for temporarily increasing the rigidity of an orthopaedic prosthesis are to be understood as mere examples of a large number of possible embodiments.

We claim:

1. A method for implanting an orthopaedic prosthesis into a patient's body, the method comprising:
    inserting a biodegradable element into a recess of a prosthetic body without plastically deforming the prosthetic body, the recess being defined by at least first and second elastic elements;
    substantially preventing deflection of the elastic elements toward each other with the biodegradable element;
    implanting the prosthetic body into the patient's body; and
    biodegrading at least a portion of the biodegradable element thereby creating space within the recess;
    wherein the implanting step comprises introducing an acetabulum into a hip joint of the patient.

2. The method of claim 1 further comprising, after the biodegrading step, allowing the first and second elastic elements to deflect towards each other into the space vacated by the biodegradable element.

3. The method of claim 1 further comprising frictionally engaging the biodegradable element with an inner surface of the recess to substantially prevent relative movement between the biodegradable element and the prosthetic body.

4. The method of claim 3 further comprising preventing the biodegradable element from extending beyond an outer surface of the support body.

5. The method of claim 1 wherein the implanting step comprises introducing a prosthetic shaft into a hollow of a bone.

6. The method of claim 1 wherein the prosthetic body is metal.

7. A method for implanting an orthopaedic prosthesis into a patient's body, the method comprising:
- inserting a biodegradable element into a recess of a prosthetic body without plastically deforming the prosthetic body, the recess being defined by at least first and second elastic elements;
- substantially preventing deflection of the elastic elements toward each other with the biodegradable element;
- implanting the prosthetic body into the patient's body; and
- biodegrading at least a portion of the biodegradable element thereby creating space within the recess; and
- wherein the prosthetic body is substantially non-bioreabsorbable.

8. A method for implanting an orthopaedic prosthesis into a patient's body comprising:
- introducing a prosthetic body into a cavity within a patient's body;
- temporarily increasing the rigidity of a portion of the prosthetic body to reduce relative movement between the prosthetic body and the inner walls of the cavity;
- anchoring the prosthetic body to the inner walls of the cavity;
- after the anchoring step, decreasing the rigidity of said portion of the prosthetic body after the prosthetic body has become substantially fixed to the inner walls of the cavity;
- inserting a biodegradable element into a recess of a prosthetic body without plastically deforming the prosthetic body, and biodegrading at least a portion of the biodegradable element thereby creating space within the recess; and
- wherein the biodegradable element is inserted into the recess before the prosthetic body is introduced into the cavity of the patient's body.

* * * * *